United States Patent
Barkóczy et al.

(10) Patent No.: US 7,098,210 B2
(45) Date of Patent: Aug. 29, 2006

(54) 2H-PYRIDAZINE-3-ONE DERIVATIVES, PHARMACEUTICAL COMPOSITIONS CONTAINING THE SAME AND A PROCESS FOR THE PREPARATION OF THE ACTIVE INGREDIENT

(75) Inventors: József Barkóczy, Budapest (HU); Péter Kótay Nagy, Vác (HU); Gyula Simig, Budapest (HU); György Lévay, Budakeszi (HU); István Gacsályi, Budapest (HU); András Egyed, Budapest (HU); Judit Ráczné Bajnógel, Budapest (HU); Katalin Pallagi, Budapest (HU); Éva Schmidt, Budapest (HU); Gábor Szénási, Budapest (HU); Anikó Miklósné Kovács, Budapest (HU); János Wellmann, Budapest (HU)

(73) Assignee: Egis Gyógyszergyár Rt., Budapest (HU)

( * ) Notice: Subject to any disclaimer, the term of this patent is extended or adjusted under 35 U.S.C. 154(b) by 218 days.

(21) Appl. No.: 10/484,619

(22) PCT Filed: Jul. 24, 2002

(86) PCT No.: PCT/HU02/00072

§ 371 (c)(1),
(2), (4) Date: Apr. 23, 2004

(87) PCT Pub. No.: WO03/010166

PCT Pub. Date: Feb. 6, 2003

(65) Prior Publication Data

US 2004/0171619 A1    Sep. 2, 2004

(30) Foreign Application Priority Data

Jul. 26, 2001 (HU) .................................. 0103063

(51) Int. Cl.
*C07D 413/14* (2006.01)
*A61K 31/501* (2006.01)
*A61P 25/22* (2006.01)
*A61P 25/24* (2006.01)

(52) U.S. Cl. .................................. 514/252.03; 544/238
(58) Field of Classification Search ................ 544/238; 514/252.03

See application file for complete search history.

(56) References Cited

U.S. PATENT DOCUMENTS

| 5,034,391 A | 7/1991 | Blaschke et al. ........... 514/252 |
| 5,736,558 A | 4/1998 | Foguet et al. ............... 514/321 |

OTHER PUBLICATIONS

Strappaghetti et al, "New 3 (2H) -pyridazinone derivatives: synthesis and affinity towards alpha1AR subtypes and 5HT1A receptors", European journal of medicinal chemistry editions scientifique elsevier, Paris, FR, vol. 32, No. 4, 1997, pp. 339-342.

*Primary Examiner*—Kahsay Habte
(74) *Attorney, Agent, or Firm*—Birch, Stewart, Kolasch & Birch, LLP

(57) ABSTRACT

The invention refers to novel 2H-pyridazine-3-one derivatives of the formula I, pharmaceutical compositions containing the same and a process for the preparation of the active ingredient. The novel compounds possess neuroleptic effect and can be used, primarily, for the treatment of schizophrenia. In formula I, R stands for a hydrogen atom or a $C_{1-4}$ alkyl group, X and Y represent, independently, a hydrogen atom, a halogen atom or a group of the formula II, with the proviso that one of X and Y means always a group of the formula II, and then the other one stands for a hydrogen atom or a halogen atom, wherein in formula II n has a value of 1 or 2.

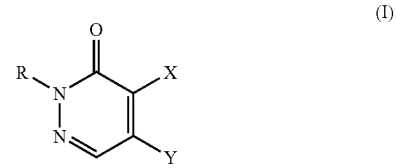

(I)

13 Claims, No Drawings

2H-PYRIDAZINE-3-ONE DERIVATIVES, PHARMACEUTICAL COMPOSITIONS CONTAINING THE SAME AND A PROCESS FOR THE PREPARATION OF THE ACTIVE INGREDIENT

FIELD OF THE INVENTION

The invention refers to novel 2H-pyridazine-3-one derivatives, pharmaceutical compositions containing the same as the active ingredient and a process for the preparation of the active ingredient. The novel compounds possess neuroleptic effect and can be used, primarily, for the treatment of schizophrenia.

BACKGROUND OF THE INVENTION

Psychiatric diseases including affective clinical patterns (schizophrenia, anxiety, depression) form a great challenge to the medical science. About 1% of the population suffers from schizophrenia. However, the recent drug therapy is not completely suitable for the treatment of the disease. Clinically, schizophrenia is characterized by two syndromes which are fundamentally different as to etiology and response to drug therapy. These are the so called positive or productive symptoms (hallucination, delusions) and negative or deficit symptoms (the emotional life becomes empty, dumbness) [Crow, T. J., Brit. Med. J., 280, 66 (1980)]. It is believed that the formation of the productive symptoms is due to the hyperfunction of the mesolimbic dopaminergic system [Kahn, R. S. and Davis, K. L., The Fourth Reneration of Progress, editor: Bloom, F. E. and Kupfer, D. J., Raves Press, New York, p 1215 (1995)], and these symptoms can be well controlled by the so called classic neuroleptics (haloperidol, chlorpromazine). However, in case of the negative symptoms, the hypofunction of the mesolimbic dopaminergic system is characteristic [Knable, M. B. and Winberger, D. M., Psychopharmacology, 11, 123 (1997)], and then the drugs mentioned above are ineffective, moreover, they can cause a deterioration of the negative symptoms. The so called conventional neuroleptics (haloperidol, chlorpromazine) which are primarily dopamine $D_2$ receptor antagonists dominate the therapy up to this time. Consequently, as mentioned above, they have numerous unfavourable side effects and are inefficient in one of the syndromes of schizophrenia (negative symptoms) [Ellenbroek, B. A., Pharmacol. Ther., 57, 1 (1993)].

After the discovery of the 5-$HT_{2A}$ receptors [Leysen et al., Biochem. Pharmacol., 27, 307 (1978)], the role of these receptors was upgraded in the therapeutical effect against schizophrenia. Clozapine was the first drug that bound to the 5-$HT_{2A}$ receptors more strongly than to the $D_2$ receptors and did not have the unfavourable side effects which characterize the conventional drugs, furthermore, clozapine controlled also the negative symptoms well [Meizer, H. Y., Schizophr. Bull., 17, 263 (1991)]. Clozapine was followed by several newer, subsequent generation neuroleptics such as olanzapine, seroquel etc., however, clozapine can be considered the standard atypical neuroleptic. Also the newer atypical drugs mentioned above are equally effective in case of the positive symptoms (hallucination, delusions) and negative ones (emptiness of the emotional life, dumbness) characterizing schizophrenia.

3-(1-substituted-4-piperidinyl)-1,2-benzisoxazole derivatives having neuroleptic activity are described in the article J. Med. Chem., 28(6), 761–769 (1985). 3(2H)-pyridazinone derivatives having antiarrhythmic effect are known from U.S. Pat. No. 5,395,934.

The aim of the invention is to prepare novel compounds having neuroleptic effect which influence both syndromes of schizophrenia favourably, are more effective than clozapine and possess neither extrapyramidal nor endocrinic side effects.

SUMMARY OF THE INVENTION

More particularly, the invention refers to novel 2H-pyridazine-3-one derivatives of the formula

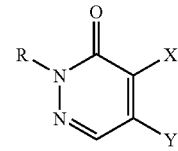

(I)

wherein
R stands for a hydrogen atom or a $C_{1-4}$ alkyl group,
X and Y represent, independently, a hydrogen atom, a halogen atom or a group of the formula

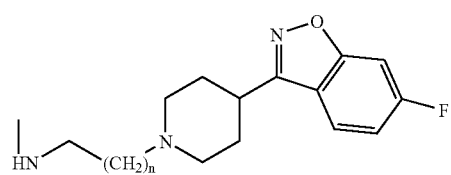

(II)

with the proviso that one of X and Y means always a group of the formula II, and then the other one stands for a hydrogen atom or a halogen atom, wherein in formula II
n has a value of 1 or 2,
and pharmaceutically suitable acid addition salts thereof.

DESCRIPTION OF THE PREFERRED EMBODIMENTS

It was found that 2H-pyridazine-3-one derivatives substituted by a (6-fluoro-1,2-benzisoxazole-3-yl)piperidine-1-ylalkylamino group have very favourable neuroleptic effect and can be used for the treatment of both syndromes of schizophrenia.

In the description and claims, a $C_{1-4}$ alkyl group is a methyl group, ethyl group, isopropyl group, n-propyl group, n-butyl group, sec.-butyl group, isobutyl group or tert.-butyl group, preferably a methyl group.

A halogen atom is a fluorine, chlorine, bromine or iodine atom, preferably a chlorine atom.

Under the pharmaceutically suitable acid addition salts of the 2H-pyridazine-3-one derivatives of the formula I, the non-toxic acid addition salts of the compounds formed with inorganic acids such as hydrochloric acid, hydrobromic acid, sulfuric acid, phosphoric acid etc. or organic acids such as formic acid, acetic acid, maleic acid, fumaric acid, lactic acid, tartaric acid, succinic acid, citric acid, benzenesulfonic acid, p-toluenesulfonic acid, methanesulfonic acid etc. are meant.

A preferred subgroup of the compounds of the invention consists of 2H-pyridazine-3-one derivatives of the formula I and pharmaceutically suitable acid addition salts thereof, wherein X represents a group of the formula II, Y stands for a hydrogen atom or a halogen atom, R and n are as defined in connection with formula I.

Within the above subgroup, the especially preferred 2H-pyridazine-3-one derivatives of the formula I and pharmaceutically suitable acid addition salts thereof are those, wherein Y stands for a hydrogen atom or a chlorine atom, R means a hydrogen atom or a methyl group, X represents a group of the formula II, wherein n is as defined in connection with formula I. Another preferred subgroup of the compounds of the invention consists of 2H-pyridazine-3-one derivatives of the formula I and pharmaceutically suitable acid addition salts thereof, wherein Y stands for a group of the formula II, X represents a hydrogen atom or a halogen atom, R and n are as defined in connection with formula I.

Within the above subgroup, the especially preferred 2H-pyridazine-3-one derivatives of the formula I and pharmaceutically suitable acid addition salts thereof are those, wherein X represents a chlorine atom, R means a methyl group, Y represents a group of the formula II, wherein n is as defined in connection with formula I.

Out of the especially preferred compounds defined above, the following ones are suitable:
    4-chloro-5-{2-[4-(6-fluoro-1,2-benzisoxazole-3-yl)piperidine-1-yl]ethylamino}-2-methyl-2H-pyridazine-3-one,
    4-chloro-5-{3-[4-(6-fluoro-1,2-benzisoxazole-3-yl)piperidine-1-yl]propyl-amino}-2-methyl-2H-pyridazine-3-one,
    and pharmaceutically suitable acid addition salts thereof.

The compounds of the invention are prepared as follows:
a) for the preparation of a 2H-pyridazine-3-one derivative of the formula I, wherein Y represents a group of the formula II, X, R and n are as defined in connection with formula I, an alkylaminopyridazine-3-one derivative of the formula

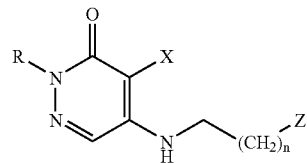

(III)

wherein Z stands for a leaving group, R, Y and n are as stated above, is reacted with 6-fluoro-3-piperidine-4-yl-1,2-benzisoxazole of the formula

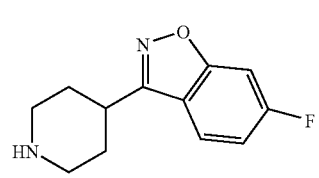

(IV)

or
b) for the preparation of a 2H-pyridazine-3-one derivative of the formula I, wherein X represents a group of the formula II, Y, R and n are as defined in connection with formula I, an alkylaminopyridazine-3-one derivative of the formula

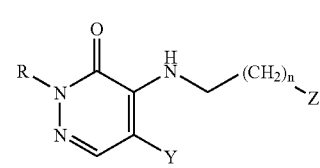

(V)

wherein Z stands for a leaving group, R, Y and n are as stated above, is reacted with 6-fluoro-3-piperidine-4-yl-1,2-benzisoxazole of the formula IV; or
c) for the the preparation of a 2H-pyridazine-3-one derivative of the formula I, wherein X stands for a halogen atom, Y represents a group of the formula II and/or Y stands for a halogen atom, X represents a group of the formula II, R and n are as defined in connection with formula I, a dihalo-pyridazine-3-one derivative of the formula

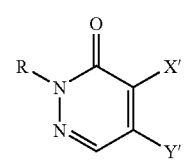

(VI)

wherein X' and Y' mean a halogen atom, R is as stated above, is reacted with a benzisoxazole derivative of the formula

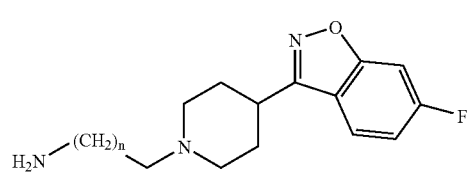

(VII)

wherein n is as stated above;
and, if desired, an obtained 2H-pyridazine-3-one derivative of the formula I is converted to a pharmaceutically suitable acid addition salt thereof or liberated from the acid addition salt thereof.

Processes a), b) and c) of the invention are carried out according to processes known from the literature [for example March, J.: Advanced Organic Chemistry, Reactions, Mechanism and Structure, 4$^{th}$ edition, John Wiley & Sons, New York, 1992]. In case of process c) of the invention, usually, a mixture of the compounds of the formula I forms i.e. a compound of the formula I, wherein X represents a group of the formula II and Y stands for a halogen atom and a compound of the formula I, wherein X stands for a halogen atom and Y represents a group of the formula II, R and n are as defined in connection with formula I depending on the starting compounds. The components of the mixture are separated by the conventional methods of the preparative organic chemistry, for example fractionated crystallization.

A 2H-pyridazine-3-one derivative of the formula I can be reacted with an inorganic or organic acid in a manner known per se to obtain a pharmaceutically suitable acid addition salt thereof or can be liberated from the acid addition salt thereof using a suitable inorganic or organic base.

The alkylaminopyridazine-3-one derivatives of the formulae III and V used as the starting substance can be prepared by the process described in the international patent application No.

The 6-fluoro-3-piperidine4-yl-1,2-benzisoxazole of the formula IV was described in the article J. Med. Chem., 28(6), 761–769 (1985).

The dihalopyridazine-3-one derivatives of the formula VI are also known [J. Chem. Soc., 1948, 2192, 2194].

The benzisoxazole derivative of the formula VII can be prepared from the 6-fluoro-3-piperidine-4-yl-1,2-benzisoxazole of the formula IV by amino-alkylation in a manner known from the literature [Arch. Pharm., 329(1), 3–10 (1996); J. Med. Chem., 28(12), 1934–1943 (1985)].

The pharmacological activity of the 2H-pyridazine-3-one derivatives of the formula I was studied on the following tests.

1. Methods Modelling Positive Symptoms 1.1 Inhibition of Conditioned Avoiding Response (CAR)

The antipsychotic (neuroleptic) effect was measured by determining the inhibition of the learned conditioned avoiding reflex. At the beginning of teaching, male Wistar rats of 120 to 150 g body weight were used for the experiments. The experimental apparatus was the so called shuttle-box consisting of two rooms of 24 cm×24.5 cm×23 cm size separated from each other by a wall. The two rooms were connected by a gate of 6 cm×9 cm size. During the test, the task of the animals was to pass from one room to the other through the gate in case of a suitable warning stimulus, thus, avoiding the punishing (unconditioned) stimulus. The warning (conditioned) stimulus appeared in the room where the animal was staying. The conditioned stimulus (CS) was a gleaming (1 Hz) white light lasting for 15 seconds. The unconditioned stimulus (US) was a randomized electric shock to the sole with an intensity of 0.6 mA which appeared in the last 5 seconds of the conditioned stimulus. Passing from one room of the shuttle-box to the other during the conditioned stimulus was considered as avoiding response, while passing during the unconditioned stimulus was considered as escaping response. Both responses stopped the actual stimulus, and the trial was finished. The intertrial interval (ITI) was 15 seconds. 80 trials were performed on a day. The learning performance was measured as the ratio of the number of the successful avoiding responses to the total number of trials in percentage. The effect of the neuroleptics was determined on the animals showing a performance of at least 75% after the stabilization of the conditioned reflex. The test compounds were administered to the rats once weekly, 1 hour before the series of experiment. When evaluating the effect of the neuroleptics in each group, the performance of the animals on the day before was used as control. From the data obtained, the 50% inhibition dose ($ID_{50}$) was determined. These values are given in Table I. Chlorpromazine [2-chloro-10-(3dimethylaminopropyl) phenothiazine] and clozapine [8-chloro-11-(4methyl-1-piperazinyl)-5H-dibenzo[b,e][1,4]diazepine] were used as the reference substance.

TABLE I

Inhibition of the conditioned avoiding response

| Compound (Example No.) | Conditioned reflex, $ID_{50}$ in mg/kg |
|---|---|
| 1 | 0.7 |
| 2 | 5.8 |
| 4 | 0.3–0.5 |
| 5 | ≦3.0 |
| chlorpromazine | 13.2 |
| clozapine | 21.3 |

The results given in Table I indicate that each tested compound of the invention inhibited the conditioned avoiding response effectively. Their efficacy surpassed that of the reference molecules by at least one order of magnitude.

1.2 Inhibition of Apomorphine Stereotypy and Climbing on Mouse

Male NMRI mice of 20 to 24 g body weight were used in the experiments. The animals were treated with the carrier and the test substance (20 ml of volume/kg body weight), respectively, then 30 minutes later, for habituation, they were placed into wire screen cages of 12 cm×12 cm×12 cm size which could be covered by plexyglass plates. After 30 minutes, 1 ml/kg of apomorphine hydrochloride were administered to the mice in a volume of 10 ml/kg, subcutaneously. The measurement of the stereotyped behaviour was begun at once after the treatment with apomorphine and continued for 25 minutes. The measurement was performed by means of a scale having five grades:

0 point: normal behaviour corresponding to that of the control animals.

1 point: permanent exploration activity, smelling or moving the head sideways from time to time.

2 points: intensive continuous head movement or smelling, periodical exploration activity.

3 points: licking, biting or gnawing from time to time, alternating with intensive smelling or head movement, locomotor activity lasting for a very short time.

4 points: continuous intensive licking and/or gnawing in the same place without any locomotor or exploration activity.

The posture when the mouse climbed up on the vertical wall with at least three legs was considered as climbing. The evaluation was performed in the last ten minutes of the observation on the basis yes/no (+/−).

Evaluation of stereotypy: in case of each animal, the highest point value obtained during the observation was taken into consideration and recorded, respectively. From the maximum point value, median was calculated for each group which was related to the median of the control group to calculate the effect in percentage. From the latter values, based on dose vs. effect relationships, the value of $ID_{50}$ (dose provoking 50% of inhibition) was calculated by linear regression.

Evaluation of climbing: when evaluating the inhibiting effect, the number of animals exhibiting climbing was taken into consideration. The frequency was calculated in each group, then the effect was determined in percentage considering the result obtained for the control group as 100%. From the effects in percentage, values of $ED_{50}$ (dose provoking inhibition in 50% of the animals) were calculated based on dose vs. effect relationships according to Litchfield and Wilcoxon [J. Pharmacol, Exp. Ther., 96, 99 (1949)].

The results obtained are summarized in Table II. In this case again chlorpromazine and clozapine were used as the reference substance.

TABLE II

Inhibition of the apomorphine induced stereotypy and climbing

| Compound (Example No.) | Inhibition of stereotypy, $ID_{50}$ in mg/kg po. | Inhibition of climbing, $ED_{50}$ in mg/kg po. |
|---|---|---|
| 1 | 0.4 | 0.3 |
| 2 | 2.0 | 0.6 |
| 3 | 1.2 | 0.8 |
| 4 | 0.2 | 0.06 |
| 5 | 2.0 | 0.6 |
| chlorpromazine | 6.8 | 6.1 |
| clozapine | 35.4 | 11.8 |

From the data of Table II it can be seen that the compounds of the invention antagonized the behaviour responses induced by apomorphine in a dosage that was lower by one or more magnitudes than that of the reference substances. Likewise the atypical clozapine, the examined novel compounds inhibited the climbing response more efficiently than the stereotypy.

2. Tests Modelling Negative Symptoms 2.1 Inhibition of Hypermotility Induced by Phencyclidine (PCP)

The experiments were carried out with a "digital motimeter" of 10 channels using one animal per channel. In each measuring place (a box of 44 cm×8 cm×10 cm size), the movement of the animal was indicated by the interruption of three parallel infrared light beams which was registered by the apparatus. 60 minutes after the peroral treatment (20 ml/kg) with the compound to be tested and the carrier, respectively, 3 mg/kg of phencyclidine [1-(1-phenylcyclohexyl)piperidine] were administered to the animals in a dose of 10 ml/kg intraperitoneally. After 15 minutes, the treated animals were placed into the apparatus, and, after 45 minutes, the number of interruptions of the infrared light beam was read at each channel. 10 mice were used in each test group. During evaluation, the average was calculated in each test group, then the effect was determined in percentage considering the average of the control group as 100%. From the effects in percentage, the values of $ID_{50}$ were calculated based on the dose vs. effect relationships by linear regression. The results obtained are shown in Table III. Haloperidol [4-(4-chlorophenyl-4-hydroxy-1-piperidinyl)-1-(4-fluorophenyl)-1-butanone] and clozapine were used as the reference substance.

TABLE III

Inhibition of hypermotility induced by phencyclidine

| Compound (Example No.) | $ID_{50}$ in mg/kg sc. |
|---|---|
| 1 | 0.4 |
| 4 | 0.07 |
| 5 | 0.46 |
| 6 | 0.9 |
| 7 | 0.4 |
| 8 | 0.2 |
| 9 | 1.4 |
| haloperidol | 1.2 |
| clozapine | 2.9 |

From Table III it can be seen that the examined compounds of the invention inhibited the increase in motor activity induced by phencyclidne much more efficiently than the reference substances.

3. Cataleptogenous Effect

The cataleptogenous effect was studied according to the method of Morpurgo [Morpurgo, C., Arch. Int. Pharmacodyn., 137, 84 (1992)]. Male Wistar rats of 220 to 240 g body weight have been used for the examinations. The fore-feet of the rats were placed on a gum stopper, one by one, and it was observed how the animal tolerated the unusual posture. The normal (non-cataleptic) animal removes the foot from the stopper during the measuring time of 10 seconds. If the animal keeps the foot on the stopper during the measuring time, this stiff state accompanied by myotonia is evaluated as catalepsy. For each compound tested, the minimum effective dosis (MED) was determined. The results obtained are shown in Table IV. Haloperidol and risperidone [3-{2-[-4-(6-fluoro-1,2-benzisoxazole-3-yl)-piperidinyl]ethyl}-6,7,8,9-tetrahydro-2-methyl-4H-pyrido[1,2-a]pyrimidine-4-one] were used as the reference substance. The ratio of the dose that induces catalepsy and the value of $ID_{50}$ characterizing the inhibition of the conditioned avoiding response (CAR) is also given in Table IV.

TABLE IV

Cataleptogenous effect

| Compound (Example No.) | MED in mg/kg po. | Ratio Cat/CAR (MED/$ID_{50}$) |
|---|---|---|
| 4 | 3 | about 6 |
| 5 | 10 | >3 |
| 6 | >30 | |
| 7 | ~30 | |
| 8 | ~10 | |
| 9 | >10 | |
| haloperidol | 1 | 1.6 |
| risperidone | 1 | 2 |

It appears from the data of Table IV that the compounds of the invention induce catalepsy in a significantly higher dose range (the difference is at least threefold) than the reference substances. The comparison of the therapeutical dose range and the doses inducing catalepsy indicates that the compounds of the formula I have a much favourable side effect profile than the reference substances.

4. Lack of Cardiotoxic Effect

The cardiotoxic effect was determined in isolated right ventricular papillary muscle of the rabbit in vitro.

Method

The modified method of Hackett et al., 1990 was used (Hacket, A. M., Mc Donald S. J., P., Schweingruber, F. and Gartwaite, S. M.: Simple in vitro method to characterize antiarrhythmic agents J. Pharmacol. Methods 23, 107–116, 1990).

The effective refractory period (ERP) was measured in isolated right ventricular papillary muscle of the rabbit in vitro.

The contractions of papillary muscle preparations obtained from New Zealand rabbits weighing 2.5–3.2 kg were evaluated. The contractions (isometrically paced at 1 Hz) were recorded by 4-channel Hugo Sachs apparatus. The effects of the test compounds or references were measured in 1 μM concentration.

The effect was considered cardiotoxic if the compound significantly (p<0.01 or p<0.001) prolonged the ERP.

The results are summarized in Table V.

TABLE V

| Test compound | % change of ERP (1 μM) |
|---|---|
| Example 4 | 11.1 ± 1.7 |
| Example 5 | 5.3 ± 0.4 |
| Example 6 | 6.1 ± 1.9 |
| Example 8 | 1.5 ± 1.5 |
| Example 9 | 0.4 ± 1.1 |
| Risperidone | 34.8 ± 4.8*** |
| Iloperidone | 31.9 ± 7.8** |

**= $p < 0.01$;
***$p < 0.001$ vs. baseline

Surprisingly the invention compounds in 1 μM concentrations had no cardiotoxic effect in spite of the fact that they contain a benzisoxazole structural part. The structurally similar reference risperidone and iloperidone showed considerable and significant cardiotoxic potential.

In summary, it can be stated that the compounds of the invention are effective in the treatment of diseases accompanied by the disorders of mental and emotional life. The novel compounds have significant therapeutical effect on both the positive and negative syndromes of schizophrenia. This is supported by the results obtained on the test measuring the conditioned avoiding response, on the interaction tests induced by apomorphine as well as the inhibition of the effect of phencyclidine. Namely, phencyclidine is able to induce psychotic symptoms on man which are very similar to the deficit symptoms of schizophrenia. Therefore, the PCP model used in the tests is especially suitable for the estimation of the effect on the negative symptoms [Steinpreis, R. E., Behav. Brain Res., 74, 1–2, 45 (1995)]. It is especially remarkable that the examined novel compounds inhibit the climbing response induced by apomorphine in a much lower dose range than the stereotype behaviour. This finding is of importance since, according to literature data, the inhibition of the apomorhine stereotypy is related to the blockade of the strial dopamine receptors, while the inhibition of climbing is related to the blockade of the dopamine receptors of the nucleus accumbens [Costall et al., Eur. J. Pharmacol., 50, 39 (1978)]. Consequently, it can be expected that the compounds of the invention will not induce extrapyramidal side effects in the therapeutical doses.

It has been found in a surprising way that the invention compounds have no cardiotoxic effect despite of the benzisoxazole structural element.

Based on the above tests, the compounds of the invention and pharmaceutically suitable acid addition salts thereof can be used as active ingredients in pharmaceutical compositions.

Furthermore, the invention refers to a pharmaceutical composition comprising a 2H-pyridazine-3-one derivative of the formula I or a pharmaceutically suitable acid addition salt thereof and one or more conventional carriers.

The pharmaceutical composition of the invention contains, in general, 0.1 to 95 per cent by mass, preferably 1 to 50 per cent by mass, suitably 5 to 30 per cent by mass of the active ingredient.

The pharmaceutical composition of the invention is suitable for peroral, parenteral, rectal or transdermal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinyl-pyrrolidone) etc.; filling agents such as lactose, glucose, starch, calcium phosphate etc.; auxiliary substances for tabletting such as magnesium stearate, talc, poly(ethylene glycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propylene glycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18$^{th}$ Edition, Mack Publishing Co., Easton, USA (1990).

The pharmaceutical composition contains dosage unit, in general. A typical dose for adult patients amounts to 0.1 to 1000 mg of the compound of the formula I or a pharmaceutically suitable acid addition salt thereof calculated for 1 kg body weight, daily. The daily dose can be administered in one or more portions. The actual dosage depends on many factors and is determined by the doctor.

The pharmaceutical composition is prepared by admixing a compound of the formula I or a pharmaceutically suitable acid addition salt thereof to one or more carrier(s), and converting the mixture obtained to a pharmaceutical composition in a manner known per se. Useful methods are known from the literature, e.g. Remington's Pharmaceutical Sciences mentioned above.

One subgroup of the pharmaceutical compositions of the invention contains a 2H-pyridazine-3-one derivative of the formula I, wherein X represents a group of the formula II,
Y stands for a hydrogen atom or a halogen atom,
R and n are as defined in connection with formula I,
or a pharmaceutically suitable acid addition salt thereof as the active ingredient.

Within this subgroup, the preferred pharmaceutical composition contains a 2H-pyridazine-3-one derivative, wherein R means a hydrogen atom or a methyl group,
Y stands for a hydrogen atom or a chlorine atom,
X and n are as stated above,
or a pharmaceutically suitable acid addition salt thereof as the active ingredient.

Another subgroup of the pharmaceutical compositions of the invention contains a 2H-pyridazine-3-one derivative of the formula I, wherein X stands for a hydrogen atom or a halogen atom,
Y represents a group of the formula II,
R and n are as defined in connection with formula I,
or a pharmaceutically suitable acid addition salt thereof as the active ingredient.

Within this subgroup, the preferred pharmaceutical composition contains a 2H-pyridazine-3-one derivative, wherein R means a hydrogen atom or a methyl group,
X stands for a hydrogen atom or a chlorine atom,
X and n are as stated above,
or a pharmaceutically suitable acid addition salt thereof as the active ingredient.

The especially preferred pharmaceutical composition contains 4-chloro-5-{2-[4-(6-fluoro-1,2-benzisoxazole-3-yl)piperidine-1-yl]ethylamino}-2-methyl-2H-pyridazine-3- one, 4-chloro-5-{3-[4-(6-fluoro-1,2-benzisoxazole-3-yl)piperidine-1-yl]propyl-amino}-2-methyl-2H-pyridazine-3-one, or pharmaceutically suitable acid addition salts thereof as the active ingredient.

The invention also refers to the use of a compound of the formula I or a pharmaceutically suitable acid addition salt thereof for the preparation of a pharmaceutical composition having neuroleptic effect.

Furthermore, the invention refers to a treatment process in which a non-toxic amount of a 2H-pyridazine-3-one derivative of the formula I or a pharmaceutically suitable acid addition salt thereof is administered to a patient suffering from a disease accompanied by the disorders of the mental and emotional life, especially schizophrenia.

The invention is further elucidated by means of the following Examples.

EXAMPLE 1

Preparation of 4-{2-[4-(6-fluoro-1,2-benzisoxazole-3-yl)piperidine-1-yl]ethyl-amino}-5-chloro-2-methyl-2H-pyridazine-3-one A mixture of 1.5 g (5.7 mmoles) of 2-[4-(6-fluoro-1,2-benzisoxazole-3-yl)piperidine-1-yl]-ethylamine, 50 cm$^3$ of dioxane, 0.93 g (5.2 mmoles) of 4,5-dichloro-2-methyl-2H-pyridazine-3-one and 1.38 g of potassium carbonate is boiled under stirring for 24 hours. Then, the reaction mixture is filtered, evaporated, and the crude product is subjected to chromatography over silica gel using a 3:1 mixture of hexane and acetone as the eluent. The fractions containing the product are combined, evaporated, the residue is suspended in diethyl ether, filtered, and dried.

Thus, 0.74 g (35.4%) of the title compound are obtained. M.p.: 108–109° C.:

Analysis for $C_{19}H_{21}ClFN_5O_2$ (405.86) calculated: C 56.23%, H 5.22%, N 17.26%, Cl 8.74%; found: C 55.80%, H 5.17%, N 16.99%, Cl 8.52%. IR (KBr): 3290, 1630,1607, 1554. $^1$H-NMR (CDCl$_3$, i400): 7.76 (m, 1H), 7.50 (s, 1H), 7.24 (dd, $J_1$=1.7 Hz, $J_2$=8.5 Hz, 1H), 7.07 (~dt, $J_d$=1.8 Hz, $J_t$=8.8 Hz, 1H), 6.47 (b, 1H), 3.91 (m, 2H), 3.73 (s, 3H), 3.08 (m, 3H), 2.72 (m, 2H), 2.31 (m, 2H), 2.03 (m, 4H). $^{13}$C-NMR (CDCl$_3$, i400): 164.07 (d, J=251.0 Hz), 163.81, 160.83, 156.37, 139.07, 122.81, 117.15, 112.37 (d, J=25.6 Hz), 97.38 (d, J=26.7 Hz), 57.44, 53.06, 40.53, 39.93, 34.34, 30.31.

EXAMPLE 2

Preparation of 4-{3-[4-(6-fluoro-1,2-benzisoxazole-3-yl)piperidine-1-yl]propyl-amino}-5-chloro-2-methyl-2H-pyridazine-3-one A mixture of 1.12 g (4 mmoles) of 4-(3-bromopropylamino)-5-chloro-2-methyl-2H-pyridazine-3-one, 20 cm$^3$ of acetonitrile, 1.05 g (4.8 mmoles) of 6-fluoro-3-piperidine-4-yl-1,2-benzisoxazole and 0.87 cm$^3$ of triethylamine is boiled under stirring for 2 hours. Then, the reaction mixture is evaporated, and, to the crude product, 30 cm$^3$ of water are added. The aqueous layer is extracted three times using 30 cm$^3$ of ethyl acetate each time. The combined organic phases are washed twice using 30 cm$^3$ of water each time and dried over anhydrous magnesium sulfate. After filtration, the organic phase is evaporated and the crude product obtained is recrystallized from 2-propanol.

Thus, 1.1 g (65.8%) of the title product are obtained. M.p.: 117–119° C.

Analysis for $C_{20}H_{23}ClFN_5O_2$ (419.89) calculated: C, 57.21%; H, 5.52%; N, 16.68%; Cl, 8.44%. found: C, 56.94%; H, 5.50%; N, 16.57%; Cl, 8.43%. IR (KBr): 3200, 1611, 1493. $^1$H-NMR (CDCl$_3$, i400): 8.16 (bdd, $J_1$=5.3 Hz, $J_2$=8.3 Hz, 1H), 7.47 (s, 1H), 7.23 (m, 2H), 7.04 (~td, $J_d$=2.1 Hz, $J_t$=8.9 Hz, 1H), 3.92 (~q, J=6.1 Hz, 2H), 3.75 (s, 3H), 3.14 (m, 3H), 2.58 (m, 2H), 2.34 (m, 2H), 2.18 (m, 2H), 2.00 (m, 2H), 1.85 (m, 2H). $^{13}$-C-NMR (CDCl$_3$, i400): 164.11 (d, J=250.6 Hz), 164.02 (d,J=13.4 Hz), 161.23, 156.48, 139.92, 139.45, 123.70 (d, J=10.7 Hz), 117.15, 112.15 (d, J=24.8 Hz), 105.82, 97.21 (d, J=26.7 Hz), 57.28, 53.73, 44.06, 39.88, 34.73, 30.01, 26.49.

EXAMPLE 3

Preparation of 4-{3-[4-(6-fluoro-1,2-benzisoxazole-3-yl)piperidine-1-yl]propyl-amino}-5-chloro-2H-pyridazine-3-one A mixture of 4.32 g (16 mmoles) of 4-(3-bromopropylamino)-5-chloro-2H-pyridazine-3-one, 80 cm$^3$ of acetone, 4.11 g (168 mmoles) of 6-fluoro-3-piperidine-4-yl-1,2-benzisoxazole, 4.48 g (32 mmoles) of potassium carbonate and 0.27 g (1.6 mmoles) of potassium iodide is boiled under stirring for 24 hours. Then, the reaction mixture is evaporated, and the crude product is subjected to chromatography over silica gel using a 1:1:0.2 mixture of hexane, ethyl acetate and methanol as the eluent. The fractions containing the product are combined, evaporated, the residue is suspended in diethyl ether, filtered, and dried.

Thus, 1.94 g (30.0%) of the title compound are obtained. M.p.: 198–200° C.

Analysis: for $C_{19}H_{21}ClFN_5O_2$: calculated: C, 56.23%; H, 5.22%; N, 17.26%; Cl, 8.74%. found: C, 55.80%; H, 5.17%; N, 16.99%; Cl, 8.52%. IR (KBr): 3348, 1615, 1494. $^1$H-NMR (CDCl$_3$, i400): 12.82 (s, 1H), 8.22 (bdd, $J_1$=5.6 Hz, $J_2$=8.2 Hz, 1H), 7.73 (d, J=8.0 Hz, 1H), 7.32 (m, 3H), 3.81 (m, 2H), 3.4–3.0 (m, 5H), 2.4–2.0 (m, 6H), 1.84 (m, 2H). $^{13}$C-NMR (CDCl$_3$, i400): 166.05 (d, J=250.3 Hz), 163.15 (d, J=14.5 Hz), 161.22, 156.94, 140.03, 139.53, 124.05 (d, J=11.1 Hz), 117.19, 112.55 (d, J=25.3 Hz), 105.43, 97.20 (d, J=27.5 Hz), 56.06, 52.95, 42.74, 33.51, 29.53, 26.73.

EXAMPLE 4

Preparation of 4-chloro-5-{2-[4-(6-fluoro-1,2-benzisoxazole-3-yl)piperidine-1-yl]ethyl-amino}-2-methyl-2H-pyridazine-3-one A mixture of 1.9 g (8.6 mmoles) of 4-chloro-5-(2-chloroethylamino)-2-methyl-2H-pyridazine-3-one, 40 cm$^3$ of acetonitrile, 2.07 g (9.4 mmoles) of 6-fluoro-3-piperidine-4-yl-1,2-benzisoxazole, 2.36 g (32 mmoles) of potassium carbonate and 0.17 g (1.6 mmoles) of potassium iodide is boiled under stirring for 24 hours. Then, the reaction mixture is filtered through a carbon bed containing magnesium sulfate, and the organic layer is evaporated. The crude product is dissolved in ethyl acetate, washed with water, and the organic layer is dried over anhydrous magnesium sulfate. After filtration, the organic phase is evaporated, and the crude product obtained is recrystallized from ethyl acetate.

Thus, 2.8 g (80.5%) of the title product are obtained. M.p.: 145–147° C.

Analysis: for $C_{19}H_{21}ClFN_5O_2$ (405.86) calculated: C, 56.23%; H, 5.22%; N, 17.26%; Cl, 8.74%. found: C, 55.73%; H, 5.26%; N, 16.98%; Cl, 8.98%. IR (KBr): 3278, 1635, 1616. $^1$H-NMR (CDCl$_3$, i400): 7.66 (dd, J$_1$=5.1 Hz, J$_2$=8.7 Hz, 1H), 7.56 (s, 1H), 7.25 (dd, J$_1$=2.1 Hz, J$_2$=8.5 Hz, 1H), 7.07 (~td, J$_d$=2.1 Hz, J$_t$=8.8 Hz, 1H), 5.62 (bt, 1H), 3.76 (s, 3H), 3.40 (~q, J=5.6 Hz, 2H), 3.13 (m, 1H), 3.04 (m, 2H), 2.75 (t, J=6.0 Hz, 2H), 2.32 (m, 2H), 2.10 (m, 4H).
$^{13}$C-NMR (CDCl$_3$, i400): 164.03 (d, J=250.6 Hz), 163.81 (d,J=13.4 Hz), 160.71, 157.75, 144.04, 125.62, 122.35 (d, J=11.1 Hz), 117.13, 112.39 (d, J=25.6 Hz), 107.40, 97.40 (d, J=27.1 Hz), 56.02, 52.92, 40.11, 39.23, 34.20, 30.48.

EXAMPLE 5

Preparation of 4-chloro-5-{3-[4-(6-fluoro-1,2-benzisoxazole-3-yl)piperidine-1-yl]propyl-amino}-2-methyl-2H-pyridazine-3-one A mixture of 2.4 g (10 mmoles) of 4-chloro-5-(2-chloropropylamino)-2-methyl-2H-pyridazine-3-one, 40 cm$^3$ of acetonitrile, 2.46 g (11 mmoles) of 6-fluoro-3-piperidine-4-yl-1,2-benzisoxazole, 2.8 g of potassium carbonate and 0.18 g of potassium iodide is boiled under stirring for 24 hours. Then, the reaction mixture is cooled to room temperature, and filtered. The filtered matter is suspended in 100 cm$^3$ of water under stirring and filtered again. The crude product filtered is recrystallized from acetonitrile.

Thus, 2.4 g (57.3%) of the title compound are obtained. M.p.: 200–202° C.

Analysis: for C$_{20}$H$_{23}$ClFN$_5$O$_2$ (419.89) calculated: C, 57.21%; H, 5.52%; N, 16.68%; Cl, 8.44%. found: C, 56.78%; H, 5.48%; N, 16.38%; Cl, 8.44%. IR (KBr): 3348, 1606. $^1$H-NMR (DMSO-d$_6$, i400): 8.00 (dd, J$_1$=5.3 Hz, J$_2$=8.7 Hz, 1H), 7.91 (s, 1H), 7.68 (dd, J$_1$=2.1 Hz, J$_2$=9.1 Hz, 1H), 7.28 (~dtm J$_d$=2.1 Hz, J$_t$=9.0 Hz, 1H), 6.94 (bt, J=5.7 Hz, 1H), 3.58 (s, 3H), 3.42 (~q, J=6.1 Hz, 2H), 3.16 (m, 1H), 3.00 (m, 2H), 2.43 (t, J=6.3 Hz, 2H), 2.07 (m, 4H), 1.89 (m, 2H), 1.74 (~qn, J=6.4 Hz, 2H). $^{13}$C-NMR (DMSO-d$_6$, i400): 163.81 (d, J=248.0 Hz), 163.15 (d, J=14.1 Hz), 161.56, 156.92, 144.84, 126.58, 123.89 (d, J=11.1 Hz), 117.44, 112.65 (d, J=25.2 Hz), 104.34, 97.27 (d, J=27.5 Hz), 56.07, 53.18, 41.66, 39.59, 33.52, 30.20, 26.08.

EXAMPLE 6

Preparation of 5-{2-[4-(6-fluoro-1,2-benzisoxazole-3-yl)piperidine-1-yl]ethyl-amino}-2-methyl-2H-pyridazine-3-one A mixture of 3.67 g (16.4 mmoles) of 5-(2-chloroethylamino)-2-methyl-2H-pyridazine-3-one, 90 cm$^3$ of acetonitrile, 4.05 g (18.4 mmoles) of 6-fluoro-3-piperidine-4-yl-1,2-benzisoxazole, 6.84 g of potassium carbonate and 0.37 g of potassium iodide is boiled under stirring for 24 hours. Then, the reaction mixture is cooled to room temperature and filtered. To the filtered matter, 100 cm$^3$ of water are added, and the aqueous phase is extracted five times using 50 cm$^3$ of dichloromethane each time. The combined organic phases are washed with water, dried over anhydrous magnesium sulfate, filtered, and evaporated under reduced pressure. The residue obtained is suspended in diethyl ether, and filtered. The crude product obtained is recrystallized from acetonitrile.

Thus, 3.4 g (55.9%) of the title compound are obtained. M.p.: 200–202° C.

Analysis: for C$_{19}$H$_{22}$FN$_5$O$_2$ (371.42) calculated: C, 61.44%; H, 5.97%; N, 18.86%. found: C, 62.00, H 5.98%; N, 18.84%. IR (KBr): 3261, 1620, 1571, 1114. $^1$H-NMR (CDCl$_3$, i400): 8.01 (dd, J$_1$=5.4 Hz, J$_2$=8.6 Hz, 1H), 7.68(dd, J$_1$=2.1 Hz, J$_2$=9.1 Hz, 1H), 7.53 (s, 1H), 7.28 (dd, J$_1$=2.1 Hz, J$_2$=8.5 Hz, 1H), 6.80 (bt, J=5.9 Hz, 1H), 5.51 (s, 1H), 3.47 (s, 3H), 3.16 (m, 1H), 3.15 (m, 2H), 3.01 (m, 2H), 2.52 (m, 2H), 2.19 (m, 2H), 2.05 (m, 2H), 1.84 (m, 2H). $^{13}$C-NMR (DMSO-d$_6$, i400): 163.80 (d, J=247.6 Hz), 163.16 (d, J=14.1 Hz), 161.52, 161.03, 149.17, 131.01, 123.95 (d, J=11.4 Hz), 117.44, 112.65 (d, J=25.2 Hz), 97.50 (d, J=27.5 Hz), 94.40, 56.11, 53.16, 39.49, 38.29, 33.54, 30.22.

EXAMPLE 7

Preparation of 5-{3-[4-(6-fluoro-1,2-benzisoxazole-3-yl)piperidine-1-yl]propyl-amino}-2-methyl-2H-pyridazine-3-one A mixture of 4.12 g (17.3 mmoles) of 5-(3-chloropropylamino)-2-methyl-2H-pyridazine-3-one hydrochloride, 100 cm$^3$ of acetonitrile, 4.29 g (19.5 mmoles) of 6-fluoro-3-piperidine-4-yl-1,2-benzisoxazole, 7.24 g of potassium carbonate and 0.39 g of potassium iodide is boiled under stirring for 24 hours. Then, the reaction mixture is cooled to room temperature, and filtered. To the filtered matter, 150 cm$^3$ of water are added, and the aqueous layer is extracted 5 times using 90 cm$^3$ of dichloromethane each time. The combined organic phases are washed with water saturated with sodium chloride, dried over magnesium sulfate, and filtered through active carbon. The organic layer is evaporated under reduced pressure, the residue obtained is suspended in diethyl ether, then filtered. The crude product is recrystallized from acetonitrile.

Thus, 4.14 g (62.2%) of the title compound are obtained. M.p.: 163–165° C.

Analysis: for C$_{20}$H$_{24}$FN$_5$O$_2$ (385.44) calculated: C, 62.32%; H, 6.28%; N, 18.17%. found: C, 62.18%; H, 6.27%; N, 18.09%. IR (KBr): 3264, 1624, 1591, 1119. $^1$H-NMR (CDCl$_3$, i400): 7.71 (dd, J$_1$=5.0 Hz, J$_2$=8.7 Hz, 1H), 7.32 (s, 1H), 7.26 (dd, J$_1$=2.1 Hz, J$_2$=8.4 Hz, 1H), 7.10 (dt, J$_d$=2.1 Hz, J$_t$=8.8 Hz, 1H), 6.48 (b, 1H), 5.65 (d, J=2.7 Hz, 1H), 3.66 (s, 3H), 3.22 (m, 5H), 2.72 (m, 2H), 2.42 (m, 2H), 2.42 (m, 4H), 1.93 (m, 2H). $^{13}$C-NMR (DMSO-d$_6$, i400): 164.26 (d, J=251.8 Hz), 164.00 (d, J=13.7 Hz), 162,23, 160.42, 148.81, 130.69, 122.29 (d, J=11.1 Hz), 117.22, 112.61 (d, J=25.2 Hz), 97.52 (d, J=26.7 Hz), 96.38, 57.21, 53.22, 42.31, 38.94, 33.70, 30.16, 23.92.

EXAMPLE 8

Preparation of 5-{2-[4-(6-fluoro-1,2-benzisoxazole-3-yl)piperidine-1-yl]ethyl-amino}-4-chloro-2H-pyridazine-3-one A mixture of 5.6 g (22.2 mmoles) of 5-(3-bromoethylamino)-4-chloro-2H-pyridazine-3-one, 16 cm$^3$ of absolute dimethylformamide, 5.62 g (25.5 mmoles) of 6-fluoro-3-piperidine-4-yl-1,2-benzisoxazole, 8.85 cm$^3$ of triethylamine and 0.44 g of potassium iodide is stirred at 60° C. for 2 hours. Then, the reaction mixture is cooled to room temperature, and a solution of 5.46 g of sodium carbonate in 50 cm$^3$ of water is added, drop by drop. The mixture is stirred for half an hour, the suspension obtained is filtered, and the matter separated by filtration is washed 3 times using 20 cm$^3$ of water each time. The crude product obtained is dissolved in a 9:1 mixture of acetonitrile and water under boiling, filtered while hot, and the mother liquor is evaporated to the third of the original volume. Then, the mother liquor is cooled with ice water and stirred for 2 hours. The crystals obtained are filtered.

Thus, 6.75 g (77.6%) of the title compound are obtained. M.p.: 229–231° C.

Analysis: for $C_{18}H_{19}ClFN_5O_2$ (391.84) calculated: C, 55.18%; H, 4.89%; Cl, 9.05%; N, 17.87%. found: C, 54.79%; H, 4.94%; Cl, 8.75%; N, 17.56%. IR (KBr): 3305, 3141, 1641, 1607. $^1$H-NMR (DMSO-$d_6$, i400): 12.58 (bs, 1H), 7.96 (dd, $J_1$=5.3 Hz, $J_2$=8.8 Hz, 1H), 7.88 (s, 1H), 7.68 (dd, $J_1$=2.1 Hz, $J_2$=9.1 Hz, 1H), 7.30 (~td, $J_d$=2.1 Hz, $J_t$=9.1 Hz, 1H), 6.42 (bt, J=5.9 Hz, 1H), 3.47 (~q, J=6.1 Hz, 2H), 3.15 (m, 1H), 3.01 (m, 2H), 2.57 (t, J=6.2 Hz, 2H), 2.23 (m, 2H), 2.02 (m, 2H), 1.80 (m, 2H). $^{13}$C-NMR (DMSO-$d_6$, i400): 163.79 (d, J=248.0 Hz), 163.18 (d, J=14.1 Hz), 161.46, 157.98, 145.28, 128.09, 127.96, 123.90 (d, J=11.0 Hz), 123.80 (d, J=8.7 Hz), 117.37 (d, J=0.8 Hz), 112.72 (d, J=24.0 Hz), 112.66 (d, J=24.8 Hz), 104.40, 97.61 (d, J=27.1 Hz), 97.45 (d, J=27.5 Hz), 57.23, 57.40, 53.12, 39.70, 33.54, 33.44, 30.40.

EXAMPLE 9

Preparation of 5-{2-[4-(6-fluoro-1,2-benzisoxazole-3-yl)piperidine-1-yl]ethyl-amino}-2H-pyridazine-3-one A mixture of 2.72 g (12.9 mmoles) of 5-(2-chloroethylamino)-2H-pyridazine-3-one hydrochloride, 11 cm³ of absolute dimethylformamide, 5.0 g (22.7 mmoles) of 6-fluoro-3-piperidine-4-yl-1,2-benzisoxazole, 6.3 cm³ of triethylamine and 0.21 g of potassium iodide is stirred at reflux temperature for 8 hours. Then, the reaction mixture is cooled to room temperature and filtered. To the mother liquor, a solution of 2.6 g of sodium hydrogen carbonate in 40 cm³ of water are added, drop by drop. The precipitate obtained is filtered, suspended in 100 ml of dichloromethane, stirred for 30 minutes, then filtered again. The crude product obtained is recrystallized from a 4:1 mixture of water and acetonitrile. The crystals formed are filtered.

Thus, 2.98 g (64.6%) of the title compound are obtained. M.p.: 97–99° C.

Analysis: for $C_{18}H_{20}FN_5O_2$ (357.39) calculated: C, 60.49%; H, 5.64%; N, 19.60%. found: C, 59.97%; H, 5.74%; N, 19.28%. IR (KBr): 3261, 1616, 1272, 1176. $^1$H-NMR (DMSO-$d_6$, i400): 11.92 (bs, 1H), 8.00 (dd, $J_1$=5.0 Hz, $J_2$=8.8 Hz, 1H), 7.68 (dd, $J_1$=2.2 Hz, $J_2$=9.2 Hz, 1H), 7.52 (d, J=2.6 Hz, 1H), 7.28 (td, $J_d$=2.2 Hz, $J_t$=9.0 Hz, 1H), 6.84 (bt, J=5.2 Hz, 1H), 5.42 (d, J=2.4 Hz, 1H), 3.15 (m, 1H), 3.01 (m, 2H), 3.02 (m, 2H), 2.56 (t, J=6.5 Hz, 2H), 2.20 (m, 2H), 2.03 (m, 2H), 1.87 (m, 2H). $^{13}$-C-NMR (DMSO-$d_6$, i400): 163.80 (d, J=248.0 Hz), 163.16 (d, J=14.1 Hz), 162.34, 161.5, 149.43, 131.67, 123.93 (d, J=11.4 Hz), 117.42, 112.64 (d, J=25.2 Hz), 97.49 (d, J=27.1 Hz), 94.36, 56.10, 57.40, 53.16, 39.37, 33.56, 30.22.

The invention claimed is:

1. A 2H-pyridazine-3-one derivative of the formula

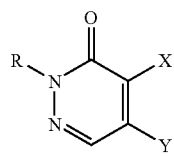

(I)

wherein

R stands for a hydrogen atom or a $C_{1-4}$ alkyl group,

X and Y represent, independently, a hydrogen atom, a halogen atom or a group of the formula

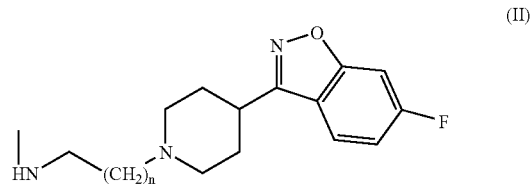

(II)

with the proviso that one of X and Y means always a group of the formula II, and then the other one stands for a hydrogen atom or a halogen atom, wherein in formula II n has a value of 1 or 2, and pharmaceutically suitable acid addition salts thereof.

2. A 2H-pyridazine-3-one derivative of the general formula I according to claim 1, wherein R stands for hydrogen or $C_{1-4}$ alkyl;

X stands for hydrogen or halogen;

Y stands for a group of the general formula II and n is 1 or 2, and pharmaceutically acceptable acid addition salts thereof.

3. Compounds according to claim 2, wherein

R stands for methyl;

X stands for chlorine;

Y stands for a group of the general formula II and n is 1 or 2, and pharmaceutically acceptable acid addition salts thereof.

4. The following compound according to claim 3:

4-chloro-5-[2-[4-(6-fluoro-1,2-benzisoxazole-3-yl)-piperidine-1-yl]-ethylamino]-2-methyl-2H-pyridazine-3-one and pharmaceutically acceptable acid addition salts thereof.

5. The following compound according to claim 3:

4-chloro-5-[3-[4-(6-fluoro-1,2-benzisoxazole-3-yl)-piperidine-1-yl]-propylamino]-2-methyl-2H-pyridazine-one and pharmaceutically acceptable acid addition salts thereof.

6. 2H-pyridazine-3-one derivatives of the formula I according to claim 1, wherein R is hydrogen or $C_{1-4}$ alkyl;

X stands for a group of the formula II;

Y stands for hydrogen or chlorine and n is 1 or 2 and pharmaceutically acceptable acid addition salts thereof.

7. 2H-pyridazine-3-one derivatives of the general formula I according to claim 6, wherein R stands for hydrogen or methyl;

X stands for a group of the formula II

Y stands for chlorine and n is 1 or 2 and pharmaceutically acceptable acid addition salts thereof.

8. A process for the preparation of a 2H-pyridazine-3-one derivative of the formula I, wherein R, X and Y are as defined in claim 1, or pharmaceutically suitable acid addition salts thereof, characterized in that a) for the preparation of a 2H-pyridazine-3-one derivative of the formula I, wherein Y represents a group of the formula II, X, R and n are as defined in connection with formula I, an alkylaminopyridazine-3-one derivative of the formula

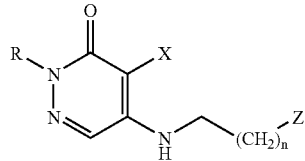
(III)

wherein Z stands for a leaving group, R, X and n are as stated above, is reacted with 6-fluoro-3-piperidine4-yl-1,2-benzisoxazole of the formula

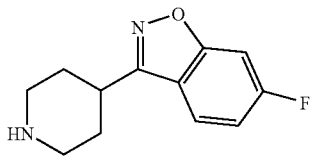
(IV)

or b) for the preparation of a 2H-pyridazine-3-one derivative of the formula I, wherein X represents a group of the formula II, Y, R and n are as defined in connection with formula I, an alkylaminopyridazine-3-one derivative of the formula

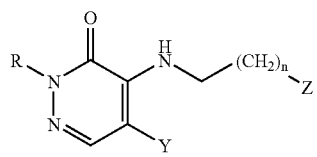
(V)

wherein Z stands for a leaving group, R, Y and n are as stated above, is reacted with 6-fluoro-3-piperidine-4-yl-1,2-benzisoxazole of the formula IV; or c) for the preparation of a 2H-pyridazine-3-one derivative of the formula I, wherein X stands for a halogen atom, Y represents a group of the formula II and/or Y stands for a halogen atom, X represents a group of the formula II, R and n are as defined in connection with formula I, a dihalo-pyridazine-3-one derivative of the formula

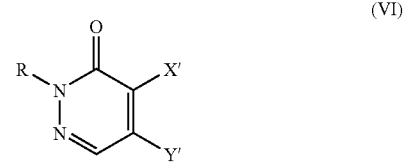
(VI)

wherein X' and Y' mean a halogen atom, R is as stated above, is reacted with a benzisoxazole derivative of the formula

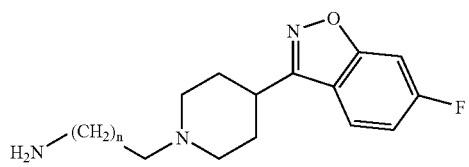
(VII)

wherein n is as stated above;

and, if desired, an obtained 2H-pyridazine-3-one derivative of the formula I is converted to a pharmaceutically suitable acid addition salt thereof or liberated from the acid addition salt thereof.

9. A pharmaceutical composition comprising a 2H-pyridazine-3-one derivative of the formula I, wherein n, R, X and Y are as defined in claim 1, or a pharmaceutically suitable acid addition salt thereof in addition to the conventional carrier(s).

10. A pharmaceutical composition according to claim 9 comprising a 2H-pyridazine-3-one derivative of the formula I, wherein R stands for hydrogen or $C_{1-4}$ alkyl; X stands for hydrogen or halogen; Y stands for a group of the formula II and n is 1 or 2, or a pharmaceutically suitable acid addition salt thereof as the active ingredient.

11. A pharmaceutical composition according to claim 10 comprising a 2H-pyridazine-3-one derivative of the formula I, wherein R stands for methyl; X stands for chlorine; Y stands for a group of the formula II and n is 1 or 2, or a pharmaceutically suitable acid addition salt thereof as the active ingredient.

12. A pharmaceutical composition according to claim 9 comprising 4-chloro-5-[2-[4-(6-fluoro-1,2-benzisoxazole-3-yl)-piperidine-1-yl]-ethylamino]-2-methyl-2H-pyridazine-3-one or a pharmaceutically suitable acid addition salt thereof as the active ingredient.

13. A pharmaceutical composition according to claim 9 comprising 4-chloro-5-[3-[4-(6-fluoro-1,2-benzisoxazole-3-yl)-piperidine-1-yl]-propylamino]-2-methyl-2H-pyridazine-one or a pharmaceutically suitable acid addition salt thereof as the active ingredient.

* * * * *